US00PP37849P2

(12) United States Plant Patent
Adrianus Maria Schoenmakers

(10) Patent No.: US PP37,849 P2
(45) Date of Patent: Nov. 17, 2026

(54) ***FITTONIA* PLANT NAMED 'KEJAPA110'**

(50) Latin Name: ***Fittonia albivenis.* (Verschaffeltii Group)**
Varietal Denomination: KEJAPA110

(71) Applicant: Schoenmakers Tussenholding B.V., Haaren (NL)

(72) Inventor: Jan Cornelis Adrianus Maria Schoenmakers, Haaren (NL)

(73) Assignee: Schoenmakers Tussenholding B.V., Haaren (NL)

( * ) Notice: Subject to any disclaimer, the term of this patent is extended or adjusted under 35 U.S.C. 154(b) by 0 days.

(21) Appl. No.: 19/638,275

(22) Filed: Apr. 3, 2026

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

'KEJAPA110' is a new and distinctive *Fittonia* plant which is characterized by a compact, creeping growth habit, decumbent lateral branching with an abundance of small elliptic foliage, very dark green laminas with a slightly lighter shade of green centrally, and a combination of orange-red and red covering the entire network of veins, foliage with a prominent red-on-very-dark-green pinnately reticulated variegation pattern, with prolonged exposure to ultraviolet light, as well as the uniformity and stability of these characteristics from generation to generation.

3 Drawing Sheets

Latin name of the genus and species: The Latin name of the genus and species of the novel variety disclosed herein is *Fittonia verschaffeltii*, which is considered to be synonymous with *Fittonia albivenis*. (Verschaffeltii Group).

Variety denomination: The inventive variety of *Fittonia* disclosed herein has been given the variety denomination 'KEJAPA110'.

BACKGROUND OF THE INVENTION

Parentage: The claimed plant 'KEJAPA110' originated as a naturally occurring partial-plant branch mutation of *Fittonia albivenis* 'Diamond' (not patented). In October of 2008, the inventor discovered the mutation, with its unique red-on-very-dark-green pinnately reticulate foliar variegation pattern, growing amongst a cultivated population of 'Diamond' plants in a commercial greenhouse in Haaren, The Netherlands. The mutation was harvested from the parent plant and subsequently propagated by rooting stem cuttings. The resulting plants were then grown to a mature size in order to evaluate and confirm the uniformity and stability of the unique characteristics first observed. Upon confirmation, in October 2009, the inventor selected the claimed *Fittonia* plant 'KEJAPA110' for commercialization due to its unique foliage coloration that differs significantly from the parent plant.

Asexual Reproduction: Asexual reproduction of 'KEJAPA110' by way of rooting stem cuttings, was first performed in October of 2008 at a commercial greenhouse in Haaren, The Netherlands. Through thirty-three subsequent generations, the plants so produced have shown that the unique features of the instant cultivar are stable and reproduced true to type.

SUMMARY OF THE INVENTION

The cultivar 'KEJAPA110' has not been observed under all possible environmental conditions, and the phenotype may vary somewhat with variations in the instant environment such as temperature, day length, and light intensity, without, however, any variance in genotype. The following characteristics have been repeatedly observed and represent the distinguishing characteristics of the new *Fittonia* cultivar 'KEJAPA110'. These traits, in combination, distinguish 'KEJAPA110' as a new and distinct cultivar.

1. *Fittonia* 'KEJAPA110' exhibits a compact, creeping growth habit, with decumbent lateral branches bearing an abundance of small elliptic foliage with pinnately reticulate venation; and
2. *Fittonia* 'KEJAPA110' exhibits foliage with an adaxial surface that generally appears as very dark green, with a slightly lighter shade of green centrally, and a combination of orange-red and red covering the entire network of veins; and
3. With prolonged exposure to ultraviolet light, the entire network of veins of *Fittonia* 'KEJAPA110' will transition to a homogenous bright red, creating a prominent red-on-very-dark-green pinnately reticulated variegation pattern.

BRIEF DESCRIPTION OF THE FIGURES

The following photographs were taken using conventional techniques and although colors may appear different from actual colors due to light reflectance, it is as accurate as possible by conventional photographic techniques.

BOTANICAL DESCRIPTION OF THE PLANT

Figure 1:
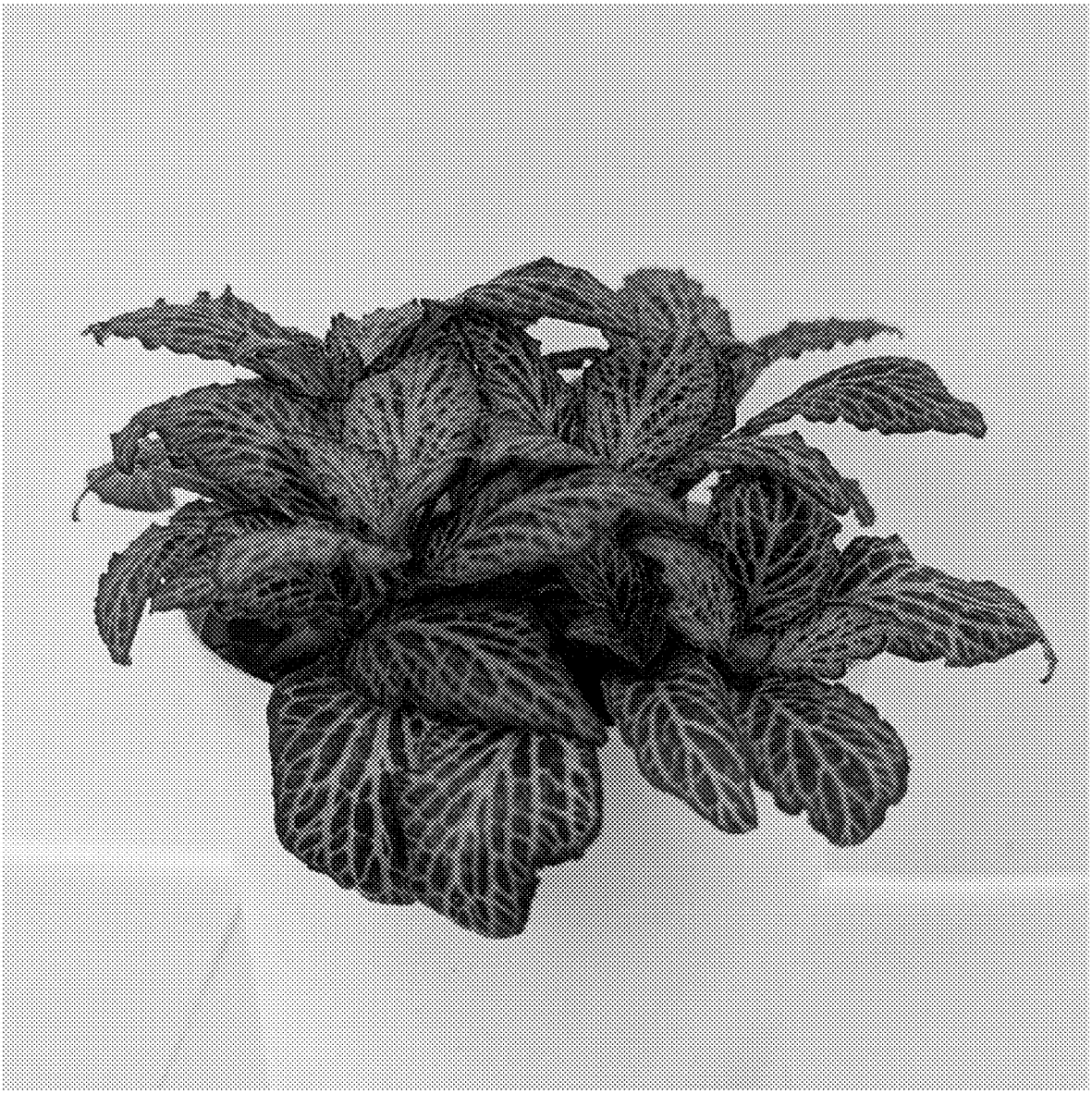
FIG. 1 shows, as nearly true as it is reasonably possible to make the same in color illustrations of this type, an exemplary plant of the new cultivar, 'KEJAPA110', approximately 15-week-old in a 350 mL nursery container. The plant shown was grown from a rooted cutting, potted into a nursery container, grown in a greenhouse in Stuarts Draft, Virginia.
Figure 2:
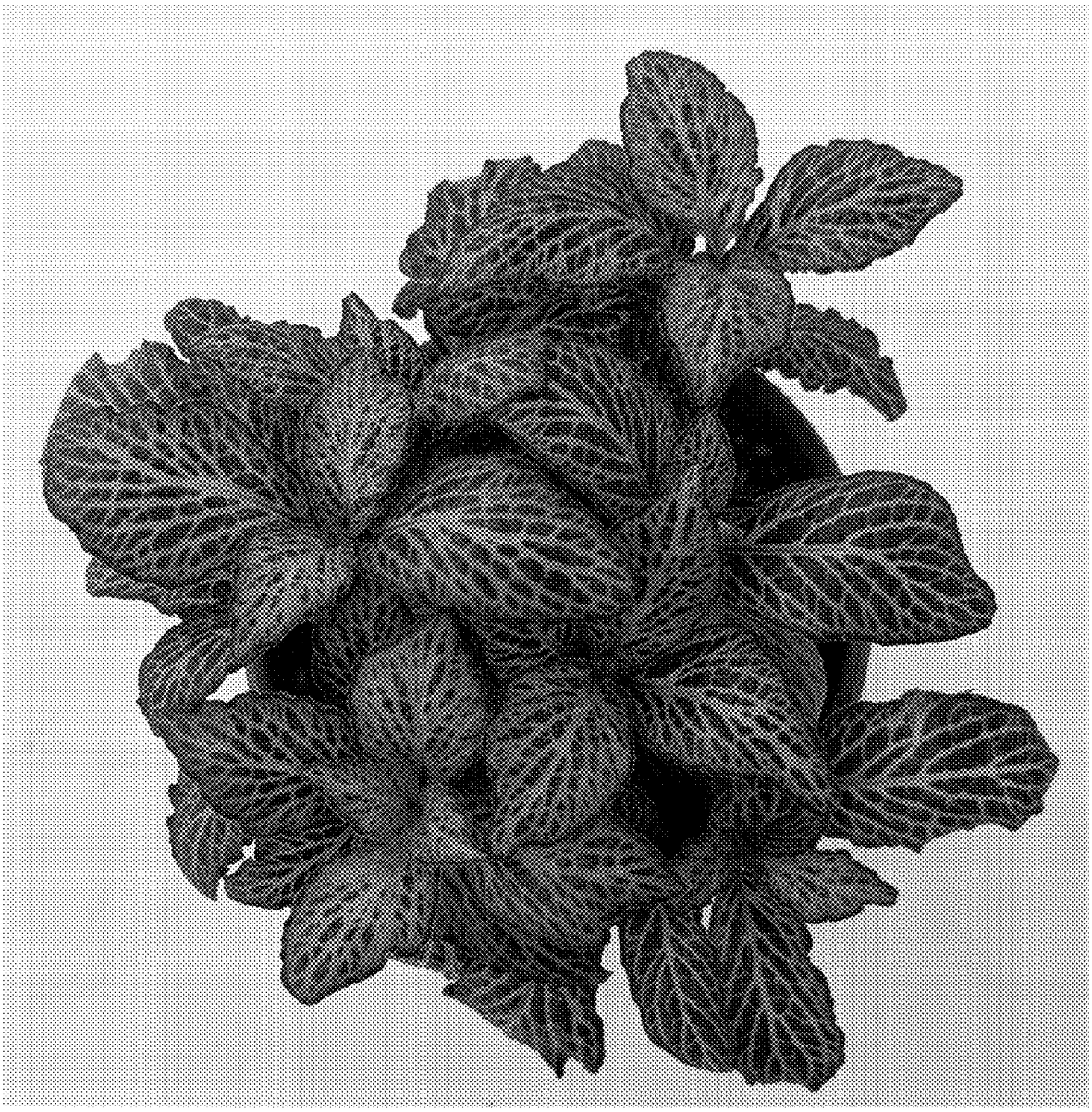
FIG. 2 illustrates the adaxial surface of the juvenile and mature foliage of 'KEJAPA110'.
Figure 3:
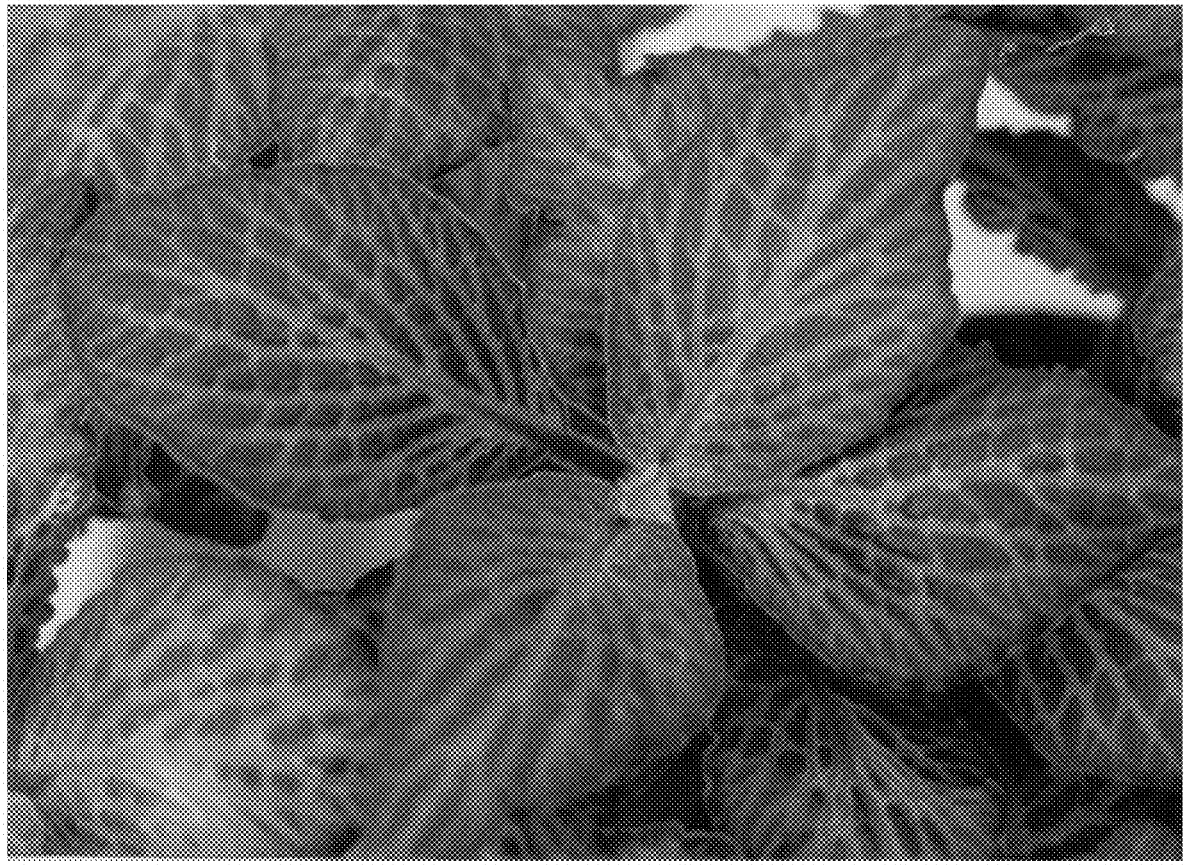
FIG. 3 illustrates the adaxial foliar surface of 'KEJAPA110' after prolonged exposure to ultraviolet light.

The following observations and measurements were made in September of 2025. With the exception of the 51-week-old plants used to describe the stoloniferous habit of the plant, the *Fittonia* 'KEJAPA110' plants described in this botanical description are approximately 13-week-old grown in a 350 mL nursery container. Plants were produced using conventional greenhouse production protocols for *Fittonia* species which consisted of overhead irrigation once a week, grown under shade with light levels ranging from approximately 2,000 to 4,000 lumens, with ambient temperatures ranging from 20 to 35 degrees Celsius and humidity levels ranging from 60 to 95 percent. No pest or disease measures were employed. The 51-week-old plants were grown in the same manner as the aforementioned 13-week-old plants, only they were moved to an outdoor area with rain exclusion and 30 percent shade at 30-weeks-old. These plants were manually watered as needed, and no pest or disease control measures were employed.

Those skilled in the art will appreciate that certain characteristics will vary with older or, conversely, with younger plants. 'KEJAPA110' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Second Edition.

A botanical description of 'KEJAPA110' and comparisons with the parent plant and the most similar variety of common knowledge are provided below.

Plant description:

*Growth habit*.—Compact, creeping perennial.

*Height*.—8.2 cm.

*Width*.—16.4 cm.

*Propagation*.—Type — Asexual propagation is accomplished by way of rooting stem cuttings. Time to produce a rooted cutting — Approximately 4 weeks to produce a rooted cutting. Time to produce a rooted mature plant — Approximately 14 to 20 weeks grown in a 350 mL nursery container.

*Disease resistance*.—'KEJAPA110' exhibits susceptibility in common with the parent including bacterial leaf spot caused by *Xanthomonas campestris*, fungal blight caused by *Rhizoctonia solani*, as well as common arthropod pests such as aphids, moths, fungus gnats, and thrips.

*Environmental tolerances*.—Adapt to temperatures as high as 31 degrees Celsius. Thrives in partial shade with 60 to 70 percent humidity. Leaf scorch may occur in direct sunlight. 'KEJAPA110' requires irrigation once every 5 to 7 days and prefers growing under 50 umol/m2/s shaded light.

Root system:

*General*.—Shallow, fibrous root system; stoloniferous.

*Texture*.—Smooth and glabrous.

*Color*.—Grey-brown, nearest to RHS 199C.

Stem:

*General branching habit*.—Basally branching main stems; with decumbent lateral branches that root at the nodes when in contact with the soil.

*Main stem*.—Length — 6.8 cm. Diameter — 0.4 cm. Internode length — 1.6 cm. Texture — Coriaceous and pubescent, with white trichomes present, closest to RHS 155A; trichomes are approximately 0.7 mm in length. Luster — Matte. Color of developing stems — Green, RHS 143C. Color of mature stems — Green, RHS 143C with light suffusion of 135A.

*Lateral branches*.—Length — 6.4 cm. Diameter — 0.4 cm. Internode length — 1.3 cm. Attitude — Decumbent. Cross-section — Terete. Texture — Coriaceous and pubescent, with white trichomes present, closest to RHS 155A; trichomes are approximately 0.7 mm in length. Color at internodes — Green, RHS 143C, with a thin stripe on the adaxial surface that is greyed-red, nearest to RHS 178B. Color — Green, RHS 143C with light suffusion of 135A.

Foliage:

*Arrangement*.—Opposite.

*Attachment*.—Petiolate.

*Division*.—Simple.

*Lamina*.—Shape — Elliptic. Length — 3.4 cm. Width — 1.9 cm. Apex — Lanceolate to acute. Base — Rounded to truncate. Aspect — Concave. Attitude — Relaxed. Margin — Crenulate, slightly undulate. Texture and luster of the adaxial surface — Coriaceous and matte. Texture and luster of the abaxial surface — Coriaceous and matte with salient veins. Color — Juvenile foliage, adaxial surface — The proximal portion of the lamina near the point of attachment is nearest to a mixture of dark green and a lighter yellow-green, RHS 131A, 144A, and 144B. The lamina becomes progressively darker moving distally towards the marginal and apical zones, ultimately transitioning to a blend of black, very dark purple, and dark green; RHS 202A, 79A, and 131A. The proximal portion of the main vein is margined with a blend of orange-red and red, RHS 33B and 39C, while the distalmost portions of the lateral and reticulate tertiary veins are red, RHS 39C, ultimately transitioning RHS 51A at and near the margins and apex. With prolonged exposure to ultraviolet light, the entire network of veins will transition to red, RHS 51A, creating a prominent red-on-very-dark-green pinnately reticulated variegation pattern. Juvenile foliage, abaxial surface — Nearest to a blend of green and greyed-green, RHS 143B and 191A. Mature foliage, adaxial surface — A relatively small central portion of the lamina near the main vein is colored nearest to a mixture of dark green, dark yellow-green, and a lighter yellow-green; RHS 131A, 144A, 147A, and 144B. All other portions of the lamina are colored with a blend of black, very dark purple, and dark green; RHS 202A, 79A, and 131A. The proximal portion of the main vein is strongly suffused with black, RHS 202A, and is further margined with a blend of orange-red and red, RHS 33B and 39C, while the distal portions of the lateral and reticulate tertiary veins are red, RHS 39C, ultimately transitioning RHS 51A at and near the margins and apex. With prolonged exposure to ultraviolet light, the entire network of veins will transition to red, RHS 51A, creating a prominent red-on-very-dark-green pinnately reticulated variegation pattern. Mature foliage, abaxial surface — Green to greyed-green, nearest to a blend of RHS 143B and 191A. Venation — Pattern — Pinnately reticulate. Color — Juvenile foliage, adaxial surface — The veins themselves are indistinguishable from the surrounding laminar surface: The proximal portion of the main vein is a blend of orange-red and red, RHS 33B and 39C, while the distalmost portions of the lateral and reticulate tertiary veins are red, RHS 39C, ultimately transitioning RHS 51A at and near the margins and apex. With prolonged exposure to ultraviolet light, the entire network of veins will transition to red, RHS 51A. Juvenile foliage, abaxial surface — Green, nearest to RHS 143D. Mature foliage, adaxial surface — The proximal portion of the main vein is a blend of orange-red and red, RHS 33B and 39C, and is strongly suffused with black, RHS 202A, while the distal portions of the lateral and reticulate tertiary veins are red, RHS 39C, ultimately transitioning RHS 51A at and near the margins and apex. With prolonged exposure to ultraviolet light, the entire network of veins will transition to red, RHS 51A Mature foliage, abaxial surface — Green, nearest to RHS 143D, and lightly suffused with greyed-orange, RHS 168C, towards the margins.

*Petiole*.—Length — 1.9 cm. Diameter — 0.2 cm. Texture — Smooth; glabrous. Luster — Slightly glossy. Color, adaxial surface — Green, nearest to RHS 143C. Color, abaxial surface — Green, nearest to RHS 143C.

Inflorescence: No flowering has been observed to date.

COMPARISONS WITH THE PARENT PLANT

Plants of the new cultivar 'KEJAPA110' may be distinguished from the parent plant, *Fittonia albivenis* 'Diamond' (not patented), by the characteristics described in Table 1.

TABLE 1

Comparison between 'KEJAPA110' and 'Diamond'

| Characteristic | 'KEJAPA110' | 'Diamond' |
|---|---|---|
| Foliage size. | Smaller than 'Diamond'. | Larger than 'KEJAPA90'. |

TABLE 1-continued

Comparison between 'KEJAPA110' and 'Diamond'

| Characteristic | 'KEJAPA110' | 'Diamond' |
|---|---|---|
| Foliage shape. | Elliptic. | Broad ovate. |
| General coloration of the mature foliage, adaxial surface. | Very dark green, with a slightly lighter shade of green centrally, and a combination of orange-red and red covering the entire network of veins. | Dark green with prominent red-purple veins which are narrowly and sharply margined with red-purple. |
| Response to prolonged exposure to ultraviolet light. | The entire network of foliar venation transitions to a homogenous bright red coloration. | The entire laminar surface becomes lightly suffused with red-purple. |

COMPARISONS WITH THE MOST SIMILAR COMMERCIAL VARIETY

Plants of the new cultivar 'KEJAPA110' may be distinguished from the most similar commercial comparator known to the inventor, *Fittonia albivenis* 'KEJAPA114' (U.S. patent application Ser. No. 19/397,379), by the characteristics described in Table 2.

TABLE 2

Comparison between 'KEJAPA110' and 'KEJAPA114'

| Characteristic | 'KEJAPA110' | 'KEJAPA114' |
|---|---|---|
| Foliage shape. | Elliptic. | Oblanceolate to broadly elliptic. |
| Foliage size. | Smaller than 'KEJAPA114'. | Larger than 'KEJAPA110'. |
| General coloration, adaxial surface of the mature foliage. | Very dark green, with a slightly lighter shade of green centrally, and a combination of orange-red and red covering the entire network of veins. | Centrally mid-green and darker green towards the margins, with veins that are broadly and diffusely margined with light red, which further ages to a green-on-pink flecked variegation pattern as the foliage ages. |

That which is claimed is:

1. A new and distinct variety of *Fittonia* plant named 'KEJAPA110', substantially as described and illustrated herein.

* * * * *